United States Patent [19]

Lipscomb et al.

[11] Patent Number: 5,190,870

[45] Date of Patent: Mar. 2, 1993

[54] METHOD FOR OXIDIZING HYDROCARBONS WITH A HYDROXYLASE FROM A METHANE MONOOXYGENASE

[75] Inventors: John D. Lipscomb, Wayzata, Minn.; Brian G. Fox, Pittsburgh, Pa.

[73] Assignee: Amoco Corporation, Chicago, Ill.

[21] Appl. No.: 600,575

[22] Filed: Oct. 8, 1990

Related U.S. Application Data

[63] Continuation-in-part of Ser. No. 352,721, May 16, 1989, abandoned.

[51] Int. Cl.$^5$ .................. C12P 17/12; C12P 17/02; C12N 1/26; C12N 1/28
[52] U.S. Cl. .................. 435/155; 435/123; 435/248; 435/249; 435/157; 435/156; 435/192; 435/195; 435/132; 435/166; 204/73 R; 204/403
[58] Field of Search .............. 435/123, 248, 249, 157, 435/156, 192, 195, 132, 155, 122, 166; 204/73 R, 403

[56] References Cited

U.S. PATENT DOCUMENTS

| | | | |
|---|---|---|---|
| 4,268,630 | 5/1981 | Patel et al. | 435/148 |
| 4,269,940 | 5/1981 | Patel et al. | 435/148 |
| 4,318,784 | 3/1982 | Higgins et al. | 435/189 |
| 4,375,515 | 3/1983 | Patel et al. | 435/189 |
| 4,587,216 | 5/1986 | Patel et al. | 435/123 |

FOREIGN PATENT DOCUMENTS 244823 4/1987 German Democratic Rep. .

OTHER PUBLICATIONS

Yu et al, *Hydrogenase Measurement with* . . . , Jour. of Bact., vol. 98, No. 1, pp. 51–55, 1969.
Buge et al, *Purification and Properties of the* . . . , Biochem. J., vol. 161, pp. 333–344, 1977.
Colloy et al, *Characterization of the Second* . . . , Biochem. J., vol. 177, pp. 903–908, 1979.
Patiel, *Methane, Monooxygenase: Parification* . . . , Archives of Biochem. & Biophys., vol. 252, No. 1, pp. 229–236, 1987.
Laane et al, *Photochemical, electrochemical and* . . . , Isr. J. Chem., 28(1), pp. 17–22, 1988.
Willner et al, *Enzyme-Catalyzed Biotransformations*, Enzyme Microle. Technol., 11(8), pp. 467–483, 1989.
Toda et al., *Chemical Simulation of Biochemical* . . . , Kenkyu Hokoku-Asahi Gauasu . . . , vol. 49, pp. 123–129, 1986.
Aono et al, *Photochemical Reduction of NADPTO NADPH Ihoug. Chim. Acta. 152(1), pp. 55–59, 11(1988).*
Woodland et al, *Purification and Characterization of*. . . , Jour. of Biological Chem., 259, No. 1, pp. 53–59, 1984.
Fox et al, *Purification of a High Specific Activity*, Biochim. & Biophys. Res. Comm., vol. 154, No. 1, 1988.
Patel et al., Journal of Bacteriology, vol. 169, No. 5, pp. 2313–2317, 1987.

*Primary Examiner*—David M. Naff
*Assistant Examiner*—Mike Meller
*Attorney, Agent, or Firm*—Amoco Corporation

[57] ABSTRACT

A purified hydroxylase component of the soluble methane monooxygenase enzyme present in the bacterium *Methylosinus trichosporium* OB3b is found capable of oxidizing hydrocarbons under aerobic conditions in the presence of suitable reducing agents. The hydroxylase can be reduced by commercial reducing agents, such as sodium dithionite and photo- and electrochemical means when in the presence of electron transport components, such as methyl viologen and proflavin. The hydroxylase component can be obtained with high final specific activity when ferrous iron compounds and cysteine are included in the purification buffers used to extract the hydroxylase from bacterial cells.

46 Claims, No Drawings

METHOD FOR OXIDIZING HYDROCARBONS WITH A HYDROXYLASE FROM A METHANE MONOOXYGENASE

This is a continuation-in-part application to application Ser. No. 352,721, filed May 16, 1989 now abandoned.

BACKGROUND OF THE INVENTION

The present invention relates to novel purified hydroxylase components of methane monooxygenase enzymes found in methanotrophic bacteria, a novel process for purifying the hydroxylases and a novel process for oxidizing hydrocarbons using purified hydroxylase, molecular oxygen ($O_2$) and commercially available reducing agents.

Alkanes are among the most unreactive carbon compounds. Alkane reactions have characteristically high activation energies and often form products which are more reactive than the parent hydrocarbons. The reactions are difficult to control for selective production of intermediate and end products in high yield. The oxidation of methane is an example of the difficulties inherent in alkane reactions.

Methane reactions are of particular interest because large quantities of natural gas are located in remote areas, far from their main centers of consumption. It is expensive, however, to transport the gas to most locations where it is used. Current technology for methane conversion is based on steam reforming, followed by either the Fischer-Tropsch process or by methanol synthesis. It is hoped that more direct paths to either product—methanol or higher hydrocarbons—can be found which are more efficient, more selective and less costly. Other alkanes are also abundant and relatively inexpensive. New technologies would enable these and other hydrocarbons to be used as inexpensive feedstocks for the synthesis of commodity chemicals as well as precursors to liquid fuels.

Additionally, the increasing presence of hazardous substances such as benzene, p-xylene and substituted hydrocarbons such as trichloroethylene in waste water streams demonstrates a need for a means for converting these substances into other substances which are less hazardous or not hazardous at all. As a result, researchers have looked to a variety of means for converting hydrocarbons into other useful products.

In particular, many researchers have attempted to mimic naturally-occurring biological systems. Certain bacteria have been found which rely exclusively on methane as their source of life-sustaining carbon compounds and energy. The first and most difficult step in the processing of methane by these methanotrophic bacteria is its conversion into methyl alcohol. This conversion of methane to methanol is catalyzed by a family of enzymes now known as methane monooxygenases.

Methane monooxygenases utilize molecular oxygen as their oxygen source. Moreover, although methane is the only hydrocarbon known to sustain growth of the bacteria, methane monooxygenases are able to catalyze the oxidation of numerous saturated and unsaturated hydrocarbons. Oxidation is accomplished by forming an activated oxygen:enzyme:substrate complex charged with two electrons from a suitable donor, such as NADH. The iron in methane monooxygenases is present in the form of a $\mu$-oxo bridged binuclear iron center. Thus, the monooxygenases have two irons available for reaction. Other than the methane monooxygenases, no other proteins containing oxo bridged iron are known to catalyze oxygenase reactions.

Methanotrophic bacteria which utilize methane monooxygenases are classified as Type I or Type II based on morphological differences in their membrane-fine structure and divergence in their metabolic pathways. Both Type I and II methanotrophs are able to express methane monooxygenases that are either soluble or membrane bound. The monooxygenase that is expressed is determined by the conditions employed for bacterial growth. Little is known about the membrane-bound monooxygenases, but some of the soluble enzymes have been isolated and examined. Examples include the methane monooxygenases isolated from the Type I organism, *Methylococcus capsulatus* (Bath); the Type II organisms, *Methylobacterium organophilum* and *Methylobacterium* sp. (CRL-26); and the Type II organism, *Methylosinus trichosporium* OB3b, the study of which led to the present invention. Those examined to date appear to be similar in composition and function.

Most methane monooxygenases isolated to date are comprised of three proteins which are nominally designated in the literature as components A, B and C. Components A and C are also referred to as hydroxylase and reductase components, respectively, because of the roles they are perceived to play in bacterial oxidation. While others have isolated the components from various strains of methanotrophic bacteria, those isolated prior to the present invention are characterized by low specific activities. Woodland et al., for example, have reported a final specific activity of 72 nmol/min/mg for the hydroxylase from the Type I organism, *Methylococcus capsulatus (Bath) (J. Biol. Chem.* 259, 53-59, 1984); and Patel et al. have reported a final specific activity of 208 for the hydroxylase from the Type II organism, *Methylobacterium* sp. (CRL-26) (*J. Bact.* 169, 2313-2317, 1987). These specific activities are much less than the approximately 800 nmol/min/mg specific activity observed for in vivo oxidation of methane.

Methane monooxygenases appear to catalyze hydrocarbon oxidation in an orderly manner. Normally, the hydrocarbon to be oxidized, oxygen and donated electrons collect at various sites of the monooxygenase system before oxidation occurs. More particularly, the reductase is believed to accept donated electrons. Component B is believed to mediate the transfer of electrons from the reductase to the hydroxylase where the oxidation is believed to occur. Previous studies by Dalton and Woodland have suggested that the substrate binds to the hydroxylase (Adv. Appl. Micro. 26, 71-87, 1980; J. Biol. Chem. 259, 53-59, 1984). The suggestion remained unconfirmed, however.

All three components are reportedly required for bacterial oxidation for *Methylococcus capsulatus* (Bath) (Colby et al., Biochem. J. 177, 903-908, 1979) and *Methylosinus trichosporium* OB3b (Fos et al., Biochem. Biophys. Res. Comm. 154, 165-170, 1988) Component B is reportedly not required for bacterial oxidation by *Methylobacterium* sp. (CRL-26) (Patel et al., J. Bact. 169, 2313-2317, 1987; Patel, Arch. Biochem. Biophys. 252, 229-236, 1987) and *Methylobacterium organophilum* (Patel et al. U.S. Pat. No. 4,587,216). Patel has disclosed the use of purified hydroxylase and reductase proteins from various organisms in combination with a cofactor system comprising NADH or NADPH for oxidizing hydrocarbons (U.S. Pat. No. 4,587,216).

Some researchers have attempted to mimic oxidation by methane monooxygenases using model compounds containing binuclear iron groups. Vincent et al., for example, have disclosed the oxidation of hydrocarbons using the model complex $Fe_2O(OAc)_2Cl_2(bipy)_2$ where bipy is 2,2'-bipyridine (J. Am. Chem. Soc. 110, 6898–6900, 1988). Oxidation was accomplished using $Bu^tOOH$ and, alternatively, $O_2$ as the monooxygen transfer reagent. The latter system also employed Zn powder and glacial acetic acid as electron and proton donors. Kitajima et al. have used synthetic analogues of hemerythrin to oxidize hydrocarbons (J. Chem. Soc. Chem. Comm. 7,485–486, 1988). $O_2$ was used as the oxygen source in the presence of Zn powder and glacial acetic acid. Murch et al. have used $(Me_4N) [Fe_2L\text{-}(OAc)_2]^5$ where L is N,N'-(2-hydroxy-5-methyl-1,3-xylene)bis(N-carboxymethylglycine) (J. Amer. Chem. Soc., 108, 5027–5028, 1986). $H_2O_2$ was used as the oxygen source. However, the oxidation rates obtained using these systems are low and none have been shown capable of large scale oxidation of hydrocarbons.

Although native methane monooxygenase systems are able to oxidize hydrocarbons, they do not present viable commercial alternatives to the more conventional methods for oxidation. Native systems obtain the electrons needed for oxygen activation from such biochemicals as NADH and NADPH which are labile and expensive and, therefore, unsuitable for production at a commercial scale. Since most native systems comprise three protein components which must be bound together, they are also too complex for efficient operation at commercial scale. Similarly, the two-component system disclosed be Patel also uses expensive and labile biochemicals. Moreover, even the use of two components presents difficulties for oxidations at commercial scale.

Accordingly, it is an object of the present invention to provide a novel method for extracting novel purified hydroxylase components with high specific activity from soluble methane monooxygenases.

It is another object of the present invention to provide a novel method for oxidizing hydrocarbons. More particularly, it is an object of this invention to provide a novel method for oxidizing hydrocarbons using molecular oxygen, chemical reductants or electrochemical or photochemical means for supplying electrons in the presence of an electron transfer-mediating compound, such as methyl viologen, and the purified hydroxylases obtained from the soluble methane monooxygenase.

It is still another object of this invention to provide a novel method for oxidizing hydrocarbons using purified, high activity hydroxylase from the methanotroph *Methylosinus trichosporium* OB3b, proflavin, methyl viologen and sodium dithionite in the absence of reductase and component B proteins.

Other objects, advantages and novel features of the invention will be apparent from the Description below.

SUMMARY OF THE INVENTION

As a class, proteins containing $\mu$-oxo bridged iron groups have not been known to catalyze oxidation reactions. The oxidation of hydrocarbons catalyzed by methane monooxygenases represents a new role for $\mu$-oxo bridged iron groups. The invention disclosed herein, therefore, relates to a new method for catalyzing the oxidation of hydrocarbons. More particularly, the invention comprises the use of hydroxylase proteins from methanotrophic bacteria possessing $\mu$-oxo bridged iron groups and commercially available reducing agents to oxidize hydrocarbons. The invention further comprises the use of novel purification protocols for obtaining novel high activity hydroxylases.

Known biochemical processes for oxidizing hydrocarbons are believed to proceed in an orderly, step-wise manner. As discussed in Background, oxidation by methane monooxygenases proceeds by the step-wise formation of a oxygen:enzyme:substrate complex charged with two electrons from a suitable donor before the oxidation takes place. In a three-component methane monooxygenase systems, the electrons are believed to be first accepted by the reductase component and then transferred to the hydroxylase component where the oxidation actually takes place. The electron transfer is believed to be mediated by the B component.

It has been found, however, that purified hydroxylase component can be separated from the monooxygenase system and used to catalyze the oxidation of hydrocarbons in the absence of the reductase and B components of the monooxygenase system. It has also been found that the key functional group of the hydroxylase for catalysis is a $\mu$-oxo bridged iron group, that both irons in the bridged group must be in the reduced (ferrous) form for catalysis to occur, and that the hydroxylase can be brought to the fully reduced form by chemical reducing agents (e.g., sodium dithionite) and electrochemical (e.g., electrochemical cell) and photochemical means (e.g., bright light from a projection lamp) for supplying electrons, when in the presence of a suitable electron transfer-mediating compound, such as methyl viologen. The novel process for oxidizing hydrocarbons of the present invention comprises contacting the purified hydroxylase of a soluble methane monooxygenase enzyme with the hydrocarbon to be oxidized in the presence of an electron source in the presence of electron transfer-mediating compound, such as methyl viologen. The novel process for oxidizing hydrocarbons is able to oxidize alkanes, alkenes, aromatic hydrocarbons, substituted hydrocarbons and mixtures thereof. The hydrocarbons methane, propane, benzene, propene and trichloroethylene are preferred substrates.

It has also been found that the hydroxylase component can be purified to particularly high specific activity and that this high activity can be attributed to high iron concentration within the hydroxylase. The high activity hydroxylase of the present invention has a final specific activity of at least about 800 nmol/min/mg. The hydroxylase typically has an iron concentration of at least about 3.5 mols iron per mol hydroxylase. A hydroxylase with a final specific activity of at least about 1000 nmol/min/mg is preferred. The preferred hydroxylase typically has an iron concentration of at least about 4.0 mols iron per mol hydroxylase.

DETAILED DESCRIPTION OF A PREFERRED EMBODIMENT

A soluble three-component methane monooxygenase from the Type II methanotroph *Methylosinus trichosporium* OB3b was purified to homogeniety. The novel purification protocols permitted preservation of most of the activity present in the intact organism throughout the purification procedure. All methane monooxygenase components were recovered in high yield and exhibit much higher activities than have been reported previously. The purified hydroxylase is capable of supporting oxidation of alkanes (including methane, alkenes, aromatic and substituted hydrocarbons in the absence of the other two monooxygenase components.

Relationship of the Stabilizers to Activity—The novel high activity hydroxylase of the present invention was obtained from *Methylosinus trichosporium* OB3b using a novel purification protocol. The protocol makes use of stabilizers which have been used in the purification of other oxygenases but which had never been used in the purification of methane monooxygenases. The stabilizers comprise ferrous iron ($Fe^{2+}$) containing compounds and cysteine. The stabilizers provide a source of iron for the purified hydroxylase that is otherwise lost during purification and facilitates retention of the structural integrity of the hydroxylase as well. Ferrous ammonium sulfate is the preferred iron containing compound. Addition of these stabilizers to buffer solutions used in the purification of the hydroxylase results in significant improvement in the specific activity of the hydroxylase as well as an increase in iron content from ~2 irons per hydroxylase as previously observed to ~4 as is routinely observed in the most active hydroxylase preparations of the present invention.

The Role of the Hydroxylase Metal Center—The hydroxylase contains a spin-coupled binuclear iron cluster with a bridging oxo or hydroxo ligand (Fox et al., J. Biol. Chem. 263, 10553–10556, 1988; Woodland et al., Biochim. Biophys. Acta 873, 237–242, 1986; Prince et al., Biochim. Biophys. Acta 952, 220–229, 1988; Ericson et al., J. Amer. Chem. Soc. 110, 2330–2332, 1988). Single turnover and EPR results show that the mixed valent state ($Fe^{2+}$-$Fe^{3+}$) is unreactive toward $O_2$ on the time scale of the catalytic process. This also appears to be the case for the mixed valent state of the hydroxylase from *Methylococcus capsulatus* (Bath) and other proteins.

Relationship of the Hydroxylase Iron Center to Activity—Previous preparations of the hydroxylase form other bacteria were reported to contain approximately one binuclear iron cluster per mol (Woodland et al., J. Biol. Chem. 259, 53–59, 1984; Patel et al., J. Bact. 169, 2313–2317, 1987). Similarly, low activity preparations of the *Methylosinus trichosporium* OB3b hydroxylase presented here contained 0.8–1 cluster per mol on average. However, as indicated in Table III, high activity preparations of the OB3b hydroxylase contained substantially greater amounts of iron clusters per mol hydroxylase. In the most extreme case, an increase of approximately 2-fold in the iron cluster concentration corresponded to an increase in specific activity of about 25-fold. Since iron is present in the high activity hydroxylase only in the form of a binuclear iron cluster, this strongly implies that the iron clusters are involved in catalysis (Fox et al., J. Biol. Chem. 263, 10553–10556, 1988).

A novel high activity hydroxylase of the present invention was purified and characterized as follows:

Bacterial Growth—*Methylosinus trichosporium* OB3b was provided by Dr. R. S. Hanson (University of Minnesota) and maintained under methane and air (1:3 v/v) as described by Cornish et al. (J. Gen. Micro. 130, 2565–2575, 1984). The concentration of $FeSO_4 \cdot 7H_2O$ was increased to 80 $\mu$M during large scale growth. The cells were grown at 28°–32° C. in continuous culture (dilution=0.05 $h^{-1}$). Commercial grade methane from Air Products, Allentown, Pa., was used as the sole carbon source. A New Brunswick CFS-314 fermentor vessel was used and sparged at the following rates: methane, 600–1500 ml/min, 15 psig; air, 2500–4500 ml/min, 15 psig. Cells were harvested using an HPK 40 Pellicon cassette system equipped with 5 ft$^2$ of 0.45$\mu$ HVLP membrane (Millipore Corp., Bedford, Mass.), washed with cold 20 mM sodium phosphate buffer, pH 7, and centrifuged at 9000×g for 20 min. The cell paste was stored at −80° C. Typically, 18–25 g of cell paste per liter of culture media gave high enzyme activity.

Enzyme Assays—Assays of bacterial cells were performed at 30° C. using cells harvested directly from the fermentor vessel. Methane oxidation was measured by gas chromatography by monitoring depletion of methane from the headspace of 30 ml reaction vials. Oxygen consumption was measured polarographically as described by Arciero et al. (J. Biol. Chem. 258, 14981–14991, 1983). The bacterial suspension was supplemented with 100 $\mu$M formaldehyde before gas chromatographic assays for conversion of propene to propene oxide in order to allow adequate regeneration of NADH by endogenous formaldehyde and formate dehydrogenases. Gas chromatographic and polarographic assays of the methane monooxygenase system were performed as described by Fox et al. (Biochem. Biophys. Res. Comm. 154, 165–170, 1988). Unless explicitly stated, the specific activity values reported for the enzyme components are those observed during the hydroxylation reaction in the presence of optimal concentrations of the other components of the methane monooxygenase. The optimal concentrations were determined by varying the concentration of one component relative to fixed concentrations of the other two components. In routine polarographic assays of methane monooxygenase activity, furan is an acceptable substrate with characteristics which facilitate the assay. Furan is a water soluble liquid (64 mM at 30° C.) which is highly susceptible to oxidation. For the complete methane monooxygenase, furan has $K_{M(app)}=20$ $\mu$M and turnover number=7.6 $S^{-1}$ relative to the hydroxylase. (For purposes of the present invention, turnover number is the number of catalytic cycles per second per molecule.) Solutions of furan were standardized by gas chromatography as described by Nicholson et al. (Anal. Chem. 49, 814–819, 1977). Column fractions were screened for reductase activity by observing the catalyzed reduction of 2,6-dichlorophenol indophenol in the presence of NADH at 600 nm ($\epsilon_{600}=13$ mM$^{-1}$cm$^{-1}$) (Hultquist, D. E., Meth. Enz. 52, 463–473, 1978). A typical assay contains 50 mM MOPS (3-(N-morpholino)propane sulfonic acid), pH 7, 100 $\mu$M 2,6-dichlorophenol indophenol, 1 mM NADH, and 0.3–3 nmol reductase in a total volume of 1 ml.

Preparation of the Cell Free Extract—The cell paste (300 g) was suspended in 200 ml of 25 mM MOPS, pH 7.0, containing 200 $\mu$M $Fe(NH_4)_2(SO_4)_2 \cdot 6H_2O$, and 2 mM cysteine (buffer A). The cells were sonicated at intervals for a total of 16 min with sufficient cooling to maintain the temperature below 4° C. The sonicated suspension was diluted with an additional 200 ml of buffer A and centrifuged at 48000×g for 90 min. The supernatant was carefully decanted, diluted with an additional 200 ml of buffer A, and adjusted to pH 7.0. The diluted supernatant is called the cell free extract.

Separation of the Components of the Methane Monooxygenase—The cell free extract was immediately loaded onto a fast flow DEAE Sepharose CL-6B column (40 mm×250 mm) equilibrated with freshly prepared buffer A at a linear flow rate of 40 cm/h. After loading, the column was washed with an additional 600 ml of buffer A. All methane monooxygenase components were completely adsorbed under these conditions. The methane monooxygenase components were eluted with a 2 l gradient of 0.0–0.14M NaCl in buffer A at a linear flow rate of 15 cm/h. Fractions containing the hydroxylase, component B, and the reductase eluted at 0.075M NaCl, 0.18M NaCl, and 0.27M NaCl, respectively. Table I is a summary of the purification of the methane monooxygenase into its components.

Purification of the Hydroxylase—Pooled hydroxylase factions were immediately concentrated by ultrafiltration. The concentrated protein was applied immediately to a Sephacryl S-300 column (40 mm×950 mm) equilibrated in 25 mM MOPS, pH 7.0 containing 100 µM $Fe(NH_4)_2(SO_4)_2 \cdot 6H_2O$, 2 mM cysteine, 1 mM dithiothreitol, and 5% (v/v) glycerol at a linear flow rate of 6 cm/h. Hydroxylase fractions were pooled, concentrated via ultrafiltration, frozen in liquid nitrogen, and stored at −80° C.

Purification of Component B—Solid $(NH_4)_2SO_4$ was added to the pooled component B fractions to make a 50% saturated solution at 4° C. After 20 min, the solution was centrifuged at 30000×g for 30 min. The pellet was suspended in 25 mM MOPS, pH 7.0 and applied to a Sephadex G-50 column (40 mm×950 mm) equilibrated in the same buffer at a linear flow rate of 3 cm/h. The pooled fractions of component B were then applied to a fast flow DEAE Sepharose CL-6B column (23 mm×80 mm) equilibrated in 25 mM MOPS, pH 6.5. Component B was eluted with a 500 ml gradient from 0.08–0.25M NaCl in the same buffer at a linear flow rate of 4 cm/h. Component B fractions were pooled, concentrated via ultrafiltration, frozen in liquid nitrogen, and stored at −80° C.

Purification of the Reductase—Pooled reductase fractions were diluted with an equal volume of 25 mM MOPS, pH 6.5 containing 5 mM sodium mercaptoacetic acid. The solution was then adjusted to pH 6.5 and applied to a fast flow DEAE Sepharose CL-6B column (23 mm×80 mm) equilibrated in the same buffer. The column was washed with 100 ml of equilibration buffer containing 0.15M NaCl at a flow rate of 30 cm/h. A 500 ml gradient from 0.15–0.32M NaCl was then applied to the column at a linear flow rate of 5 cm/h. The pooled fractions were concentrated using a fast flow DEAE Sepharose CL-6B column (6 mm×15 mm). The concentrated reductase was applied to an Ultrogel AcA-54 column (25 mm×450 mm) equilibrated in 25 mM MOPS, pH 7.0, containing 5 mM mercaptoacetic acid and eluted at a linear flow rate of 3 cm/h. Fractions exhibiting a constant $A_{458}/A_{340}$ ratio of 1.3 hydroxylation activity greater than 20% of the peak fraction were pooled, concentrated using DEAE Sepharose CL-6B, frozen in liquid nitrogen, and stored at −80° C.

Molecular Weight Determinations—Ultracentrifugation experiments were performed using a Beckman Model E Series 400 ultracentrifuge with an An-D rotor using schlieren optical visualization. Sedimentation equilibrium experiments were performed according to the method of meniscus depletion as described by Yphantis (Biochemistry 3,297–317, 1970). The following conditions were used for meniscus depletion experiments: hydroxylase (protein concentration 0.6 mg/ml, density 1.01 g/ml, viscosity 1.0 ml/g, estimated $v_o$ 0.73, 15220 rpm, 12.5° C.); component B (protein concentration 1.5 mg/ml, density 0.9997 g/ml, viscosity 1.0 ml/g, estimated $v_o$ 0.73, 20410 rpm, 12.4° C.); reductase (protein concentration 1.7 mg/ml, density 1.004 g/ml, viscosity 1.0 ml/g, estimated $v_o$ 0.74, 12590 rpm, 10.5° C.).

Sedimentation velocity experiments were performed as described in Schachman (Meth. Enz. 4, 32–103, 1957). The following conditions were used for sedimentation velocity experiments: hydroxylase (protein concentration 3.33 mg/ml, density 1.01 g/ml, viscosity 1.0 ml/g, estimated $v_o$ 0.73, 25600 rpm, 6° C.); component B (protein concentration 2.2 mg/ml, density 0.9997 g/ml, viscosity 1.0 ml/g, estimated $v_o$ 0.73, 44800 rpm, 6° C.); reductase (protein concentration 1.6 mg/ml, density 1.004 g/ml, viscosity 1.0 ml/g, estimated $v_o$ 0.74, 25000 rpm, 6° C.). The partial specific volume values were determined from amino acid analysis by the Department of Biochemistry, University of Minnesota. Native molecular weights and estimation of the Stokes radii were also determined by gel filtration (Yamaguchi et al., J. Biol. Chem. 253, 8848–8853, 1978). Denaturing polyacrylamide gel electrophoresis was done as reported in Laemmli (Nature 227, 680–685, 1970).

Other Methods—Protein concentrations were determined colorimetrically using dialyzed and lyophilized samples of the purified proteins as standards as reported by Bradford (Anal. Biochem. 72, 248–254, 1976). The concentrations of the purified proteins were also determined using quantitative amino acid analysis from which extinction coefficients at 280 nm were calculated. Iron was determined spectrophotometrically by complexation with 2,4,5-tripyridyl-s-trizine (Fischer et al., Clin. Chem. 10, 21–25, 1964). Iron and other metals were also determined by inductively coupled plasma emission spectroscopy by the Soil Science Services, university of Minnesota, St. Paul. Flavin identity and content were determined by reverse phase high pressure liquid chromatography with a 0 to 50% methanol gradient in 5 mM ammonium acetate, pH 6.0 (Hausinger et al., Meth. Enz. 122, 199–209, 1986). Flavin content was also determined optically ($\epsilon_{450}=11.3$ mM$^{-1}$cm$^{-1}$) after precipitation of the reductase using trichloroacetic acid. Inorganic sulfide was determined by the method of Beinert (Anal. Biochem. 131, 373–378, 1983). Hydrogen peroxide and $O_2$ were determined by catalase or superoxide dismutase coupled $O_2$ evolution, respectively. Chromatofocusing was performed using Polybuffer exchanger PBE94 with Polybuffer 74 (Pharmacia, Piscataway, N.J.). Protein molecular weight standards, MES, MOPS, NADH, dithiothreitol, cysteine, phenazine methosulfate, proflavin, and methyl viologen were obtained from Sigma (St. Louis, Mo.). Residual ethanol (an inhibitor of the hydroxylation reaction) was removed from NADH by repeated evaporation from MOPS buffer. All other chemicals were of the best quality available and were used without further purification.

Purified Methane Monooxygenase Components—Methane monooxygenase activity is reproducibly observed in cell free extracts of *Methylosinus trichosporium* OB3b prepared as described above. This activity is fully soluble and represents all of the methane monooxygenase activity observed in the intact organisms. The activity of the cell free extract varies significantly from preparation to preparation suggesting that the cells are very sensitive to growth conditions. The overall specific activity was found to range from 20–80 nmol/min/mg when assayed without the addition of supplemental methane monooxygenase components. By adding optimal amounts of two of the purified methane monooxygenase components while assaying for the third component in the cell free extract, the specific activities of the single components are found to be 20-80 nmol/min/mg for the reductase and 50-200 nmol/min/mg for the hydroxylase and component B. Each of the components have been purified in high yield and high specific activity as described above. The results of representative purifications of the three methane monooxygenase components are summarized in Table I. The physical data obtained for the components are shown in Table II, where analogous data for the previously reported soluble methane monooxygenase systems is also presented for comparison.

Properties of the Hydroxylase—Physical properties of all three monooxygenase components are presented in Table II. The hydroxylase obtained by the two-step chromatographic procedure shown in Table I is pure as judged by repeated gel filtration, ultracentrifugation, and denaturing gel electrophoresis. In particular, there is no evidence for contamination by either of the two other monooxygenase components. For example, antibodies were raised to the purified component B and reductase, but were not observed to cross-react with the purified hydroxylase preparations. The molecular weight determined by analytical ultracentrifugation if 245 kDa. Native gel electrophoresis indicates that a single protein component is present in the purified samples. Denaturing gel electrophoresis shows that the protein consists of three subunit types with molecular weights of about 54.4, 43.0, and 22.7 kDa, suggesting that the quaternary structure is $(\alpha\beta\gamma)_2$ as observed for all other purified methane monooxygenase hydroxylase components. As shown in Table II, the maximal specific activity of the hydroxylase isolated from *Methylosinus trichosporium* OB3b using the procedures described above (1700 nmol/min/mg) is 8-25 times higher than the specific activities of hydroxylase components purified from other methanotrophs.

The oxidized form of the hydroxylase exhibits an electronic absorption maximum at 282 nm and a very weak absorption which decreases smoothly through the visible region. No distinct features are observed above 300 nm. Similarly, no optical spectrum above 300 nm is observed for either the partially or the fully reduced forms of the hydroxylase. Other hydroxylase preparations have been reported by Woodland et al. (J. Biol. Chem. 259, 53-59, 1984) and Patel et al. (J. Bact. 169, 2313-2317, 1987). In contrast to these other preparations, no absorption is observed in the regions near 410 nm and 550 nm in any oxidation state. In other proteins containing $\mu$-oxo bridged iron clusters, absorbance maxima near 410 and 550 nm have been associated with tyrosine radical formation and tyrosine ligation, respectively (Atkin et al., J. Biol. Chem. 248, 7464-7472, 1973; Averill et al., J. Amer. Chem. Soc. 109, 3760-3767, 1987). The 8.5-fold increase in specific activity obtained during the purification indicates that the hydroxylase from *Methylosinus trichosporium* OB3b comprises roughly 12% of the soluble protein, a number supported by the 8% recovery of total protein as hydroxylase. Inductively coupled plasma emission spectroscopy performed on the purified hydroxylase indicates that iron is the only metal present in stoichiometric amounts of greater.

Properties of the Reductase—The monomeric reductase from *Methylosinus trichosporium* OB3b has a molecular weight of about 39.7 kDa as measured by analytical ultracentrifugation, quantitative gel chromatography and denaturing gel electrophoresis. The reductase was found to contain 1 mol FAD per mol reductase. The ratio of iron to inorganic sulfide (Table II) and the optical spectral properties are consistent with the presence of a [2Fe-2S] cluster as has been observed for the reductase purified from other bacteria (Colby et al., Biochem. J. 177, 903-908, 1979; Patel, R. N., Arch. Biochem. Biophys. 252, 229-236, 1987). The reductase has a specific activity of 26100 nmol/min/mg for the hydroxylation reaction catalyzed by the complete methane monooxygenase. This value is approximately four times that reported for the reductase purified from other methanotrophs. The purified reductase also catalyzes the reduction of 2,6-dichlorophenol indophenol at pH 7.0 with a specific activity of 127 $\mu$mol/min/mg. The yield and the fold purification obtained suggest that the reductase accounts for approximately 0.1 to 0.3% of the soluble protein present in the cell free extract. Thus, on a molar basis, the reductase is present in the cell at about 10% of the concentration of the other two components.

Properties of Component B—Component B from *Methylosinus trichosporium* OB3b is a monomeric protein of about 15.8 kDa molecular weight as determined by analytical ultracentrifugation and denaturing gel electrophoresis. Component B has no visible spectrum above 300 nm. The yield and the fold purification obtained suggests that component B accounts for approximately 0.5% of the soluble protein. On a molar basis, component B and the hydroxylase appear to be present in approximately equal amounts. The purification of component B shown here results in a 5-fold increase in yield and 1.5-fold increase in specific activity over the comparable protein from *Methylococcus capsulatus* (Bath) (Green et al., J. Biol. Chem. 260, 15795-15801, 1985). The other physical properties shown in Table II are quite similar to the corresponding protein from *Methylococcus capsulatus* (Bath) (Green et al., J. Biol. Chem. 260, 1579-15801, 1985).

Correlation of the Oxo Bridged Iron Cluster with Activity—The novel high activity hydroxylase of the present invention is further characterized by high iron concentration at the active site of the hydroxylase. The measurement of total iron content of the hydroxylase does not distinguish between iron present at the active site in a binuclear cluster and iron adventitiously bound to the hydroxylase surface. However, this distinction can be readily made using Mössbauer and EPR spectroscopy. Mössbauer spectroscopy provides a direct estimate of the iron present in the oxidized state of the binuclear iron cluster through quantitation of the characteristic quadrupole doublet observed at 4.2° K. (Fox et al., J. Biol. Chem. 263, 10553-10556, 1988). Mössbauer spectroscopy also allows the relative amount of iron present in each of the three possible redox states of the cluster to be determined with reasonable accuracy. Likewise, quantitation of the EPR signals from the mixed valent and fully reduced states of the binuclear cluster allows reasonable estimates of the concentration of cluster present in these states (Fox et al., Biophys. Biochem. Res. Comm. 154, 165-170, 1988; Fox et al., J. Biol. Chem. 263, 10553-10556, 1988). Since the mixed valent state must be produced by titration, the values reported in Table III for the mixed valent state are somewhat variable. Hydroxylase preparations exhibiting a 25-fold range of specific activity values have been studied. Both Mössbauer and EPR spectroscopic measurements show that the binuclear cluster concentration increases in the most active preparations of the hydroxylase. Moreover, these preparations contain greater than one binuclear cluster per mol. However, it is also clear that a wide range of specific activities are possible with little change in cluster concentration especially for samples with specific activities less than 500.

Catalysis Via the Hydroxylase

The novel process for oxidizing hydrocarbons of the present invention obtains from the discovery that the hydroxylase of the methane monooxygenase from *Methylosinus trichosporium* OB3b is able to catalyze the oxidation of hydrocarbons in the absence of the reductase and B components of the native enzyme. As demonstrated by EPR spectroscopy, the binuclear iron cluster of the hydroxylase is in the fully reduced (diferrous) state when it is catalytically competent. The hydroxylase can be brought to the fully reduced state by chemical reductants (e.g., sodium dithionite) and photochemical and electrochemical means which provide electrons needed to reduce the hydroxylase, and compounds which are able to transfer the electrons to the hydroxylase to convert it to the fully reduced state. Methyl viologen and proflavin, for example, are able to mediate the transfer of electrons to the hydroxylase.

The isolated hydroxylase was able to oxidize various hydrocarbons, including alkanes, alkenes, aromatic and substituted hydrocarbons in the presence of sodium dithionite, methyl viologen and proflavin. Experimental conditions and results were as follows:

Single Turnover Oxidation of Propane and Propene—Samples of high activity hydroxylase (1000 nmol/min/mg, 100 nmol protein) in 100 mM MOPS, pH 7.0 were supplemented with 100 $\mu$M phenazine methosulfate for conversion to the mixed valent state, or with 10 $\mu$M proflavin and 100 $\mu$M methyl viologen for conversion to the fully reduced state. The mixed valent samples were prepared in EPR tubes under anaerobic conditions and the fully reduced samples were prepared in Teflon sealed 3 ml reaction vials. Anaerobiosis was established by repeated cycles of evacuation and flushing with Ar gas that had been made oxygen-free by passage through an activated copper oxygen scrubbing trap (BASF, Inc.) as described in Arciero et al. (J. Biol. Chem. 258, 14981-14991, 1983). For the mixed valent samples, reduction was performed by addition of one equivalent of sodium dithionite (two reducing equivalents, based on the presence of two binuclear iron clusters) to the hydroxylase, while for the fully reduced samples, two equivalents of sodium dithionite (four reducing equivalents, based on the presence of two binuclear iron clusters) were added. After addition of sodium dithionite, the samples were incubated for 5 min at 30° C. No residual blue color indicative of the presence of methyl viologen radical ($\epsilon_{604}=14.4 M^{-1}cm^{-1}$) was observed, showing that excess sodium dithionite was not present. The extent of reduction in the mixed valent samples was monitored by EPR spectroscopy. After measurement of the EPR spectrum, the mixed valent samples were transferred anaerobically from the EPR tube to a 3 ml reaction vial filled with Ar. Propane or propene (3 ml) was added to the reaction vial and allowed to equilibrate for 5 min at 30° C. The reaction was started by injection of 3 ml of air into the reaction vial, followed by rapid mixing of the solution. After an appropriate time period (5 s or longer), the reaction was terminated by injection of 100 $\mu$l of chloroform followed by a brief period of vortexing. The chloroform layer was separated by centrifugation (2 min at 10800$\times$g) and analyzed for reaction product by gas chromatography. 1-Propanol was obtained from propane to a yield of 10.1% and propene was oxidized to propene oxide (40.1%) (see Table IV(A)).

Addition of component B or the reductase does not significantly change the product yield, and these components are found to be incapable of catalyzing hydroxylation alone. Hydroxylase inactivated by heat precipitation is incapable of catalyzing hydroxylation. This provides the first evidence based on catalysis that the side of the monooxygenase reaction is located on the hydroxylase component. Single turnover experiments performed using the hydroxylase reduced only to the mixed valent state as described above result in much lower yields of 1-propanol or propene oxide from propane and propene, respectively (Table IV(A)). The yields obtained are approximately those expected from the concentration of fully reduced hydroxylase unavoidably present along with the mixed valent state; thus it is probable that only the fully reduced hydroxylase is capable of hydroxylation. (This conclusion is supported by the observation that only the fully reduced hydroxylase is rapidly oxidized by oxygen.)

The product of enzymic propane hydroxylation is exclusively 1-propanol, whether catalyzed by the hydroxylase alone under single turnover conditions or by the reconstituted methane monooxygenase system. No evidence for 2-propanol, the predominant product for hydroxylation catalyzed by small molecule catalysts, was observed. (For example the model complex $Fe_2O(OAc)_2Cl_2(bipy)_2$, where OAc is acetate and bipy is 2,2'-bipyridine, catalyzes the hydroxylation of ethane, propane, and cyclohexane in the presence of t-butyl peroxide (Vincent et al., J. Am. Chem. Soc. 110, 6989-6900, 1988). The hydroxylation of propane is conducted under 90 psi propane for up to two days and yields 8.8% 2-propanol.) Thus, the enzyme catalyzed reaction retains specificity under single turnover conditions, strongly implying that the reaction is catalyzed on the enzyme surface and that the reductase and component B do not play a role in directing the catalysis chemistry. The single turnover hydroxylation reaction appears to be complete in less than 5 s, which was the minimum time in which the reactants could be mixed and the reaction stopped. Thus, the turnover number of the hydroxylase alone must be at least 0.7 $s^{-1}$ and is probably much greater. This compares well with the accurately determined turnover number of the complete system of 4.4 $s^{-1}$ measured under biological turnover conditions.

Single Turnover Oxidation of Methane—Samples of low activity hydroxylase ($\sim$160 nmol/min/mg, 340 nmol), methyl viologen (40 nmol) and proflavin (0.25 nmol) in 25 mM MOPS buffer, pH 7.5 were placed in a 3 ml reaction vial sealed with a Teflon septum and made anaerobic by repeated cycles of evacuation and flushing with $O_2$-free Ar. Methane gas was then flushed through the sealed vial for 5 min. After a further 5 min incubation period to allow the equilibration of methane into the liquid phase, a three-fold excess of sodium dithionite relative to protein concentration was added to the hydroxylase solution. This solution was allowed to incubate for 5 min at 23° C. and then 3 ml of air was injected into the vial. The contents of the vial were rapidly mixed. After $\sim$10 min, the contents of the vial were placed in a Centricon concentrator device with a YM30 membrane and spun for 30 min at 5000 rpm. The aqueous phase that passed through this membrane was analyzed for methanol using gas chromatography. The yield was 61 nmol methanol of 18% based on protein concentration (see Table IV(B)).

Multiple Turnover Oxidation of Benzene—Samples of low activity hydroxylase (~160 nmol/min/mg, 400 nmol), methyl viologen (320 nmol) and proflavin (0.5 nmol) were placed in a 3 ml reaction vial sealed with a Teflon septum and made anaerobic by repeated cycles of evacuation and flushing with $O_2$-free Ar.

The following procedure was repeated for two cycles: After ~2 min, benzene (50 μmoles) was added to the reaction mixture, mixed gently and allowed to equilibrate with protein solution for 5 min. Then an equimolar amount of sodium dithionite relative to hydroxylase concentration was added to the hydroxylase solution. This solution was allowed to incubate for 5 min at 23° C. and then 3 ml of air was injected into the vial. The contents of the vial were rapidly mixed. The reaction mixture was extracted with $CHCl_3$ and analyzed for phenol using gas chromatography. Phenol was formed at a yield of about 3.4% based on nmol phenol formed per nmol hydroxylase for each cycle (see Table IV(B)).

Multiple Turnover Oxidation of Propene—Samples of low activity hydroxylase (~155 nmol/min/mg, 340 nmol), methyl viologen (40 nmol) and proflavin (0.25 nmol) and 50 μl of 0.5M MOPS buffer, pH 7.0 were placed in a 3 ml reaction vial sealed with a Teflon septum and made anaerobic by repeated cycles of evacuation and flushing with $O_2$-free Ar. The hydroxylase specific activity after this cycle was ~151.

The following procedure was repeated for seven cycles: After ~2 min, the headspace of the vial was flushed for 2 min with propene gas at a flow rate of 2 ml/min. An equimolar amount of sodium dithionite relative to hydroxylase concentration was added to the hydroxylase solution. This solution was allowed to incubate for 5 min at 23° C., and then 3 ml of air was injected into the vial. The contents of the vial were rapidly mixed. The reaction mixture was analyzed for propene oxide by gas chromatography. The total yield after seven cycles was 533 nmol propene oxide or 156% based on protein content (see Table V). This represents about 1.6 turnovers per hydroxylase molecule present in the reaction mixture. These results also indicate that the hydroxylase can catalyze repeated oxidations without inactivation of the enzyme. As indicated in Table V the measured activity of the hydroxylase was slightly greater after the second cycle, and the product yield increased until the experiment was terminated after seven cycles.

Single Turnover Oxidation of Trichloroethylene—Low activity hydroxylase (210 nmol/min/mg, 100 nmol) and methyl viologen (40 nmol) in trichloroethylene-saturated 25 mM MOPS buffer, pH 7.5, were placed in a 3 ml reaction vial sealed with a Teflon septum. A two-fold excess of sodium dithionite relative to protein concentration was added to the hydroxylase solution. The contents of the vial were rapidly mixed, followed by the addition of 500 μl of benzene after 5 seconds. The reaction products, including trichloroethylene oxide, were extracted into benzene. Since trichloroethylene oxide is unstable, it was reacted with 4-(p-nitrobenzyl)pyridine to form a stable derivative. The yield was determined by comparing the optical spectrum of the derivatized product with the optical spectrum of the analogous derivative formed from synthetic trichloroethylene epoxide. The yield was about 6 to 8 nmol trichloroethylene oxide or about 8% based on protein concentration.

The isolated hydroxylase is also able to oxidize hydrocarbons using electrochemical means as the source of reducing electrons while in the presence an electron transporter, such as methyl viologen.

Electrochemical Oxidation of Propene—Low activity hydroxylase was used to oxidize propene to propene oxide in the presence of electrochemically reduced methyl viologen with and without the additional electron transfer mediator proflavin. Experimental conditions and results were as follows:

A sample of low activity hydroxylase (155 nmol/min/mg, 342 nmol) in 25 mM MOPS buffer, pH 7.5 was made anaerobic by repeated evacuation and reflushing with $O_2$-free Ar gas. Methyl viologen was reduced at a gold electrode under anaerobic conditions in an electrochemical cell and added anaeorbically to the hydroxylase system before each cycle until the blue color or reduced methyl viologen just persisted after a few minutes of incubation. The system was flushed with propene after which 3 ml of air was injected into the system. The contents were then rapidly mixed. The reaction mixture was analyzed for propene oxide by gas chromatography. The oxidation cycle was repeated twice more.

Propene oxide was detected as a reaction product after each cycle. The yields for each cycle were 51, 122 and 140 nmol, respectively, and the total yield was 313 nmol of the epoxide. Based on protein content, this was 92%.

Propene was also oxidized to 1,2-propene oxide as above but with the addition of proflavin to the system. The reaction system was prepared as above using 548 nmol hydroxylase and 0.5 nmol proflavin. A single cycle oxidation was performed. The yield was 340 nmol epoxide or 62% based on protein content.

The isolated hydroxylase is also able to oxidize hydrocarbons using photochemical means as the source of reducing electrons while in the presence of an electron transporter, such as methyl viologen. For example, bright light will decarboxylate glycine. When methyl viologen is present during the decarboxylation, it will accept electrons to form methyl viologen radicals. These radicals are able to transmit electrons to the hydroxylase thereby enabling it to oxidize hydrocarbons.

Photochemical Reduction of the Hydroxylase—Low activity hydroxylase (~155 nmol/min/mg, 59 nmol) in 200 μl of 0.1M MOPS containing 0.1M glycine and 1 mM methyl viologen was placed in a sealed EPR tube. The tube was wrapped in aluminum foil to protect the contents from exposure to light. Oxygen was removed from the tube by repeated evacuation and flushing with $O_2$-free argon gas as described above. EPR spectra of the oxygen-free sample showed no signal at g=15 indicating the hydroxylase was in the oxidized state. The sample was then placed in a water bath at 4° C. and exposed to bright light from a projection lamp. EPR spectra of the light irradiated sample showed the signal at g=15, characteristic of the fully reduced hydroxylase. The hydroxylase is able to oxidize hydrocarbons in this state.

That which is claimed is:

1. A method for oxidizing hydrocarbons with purified hydroxylase component from a soluble methane monooxygenase comprising contacting said purified hydroxylase with said hydrocarbons in the presence of a source of electrons and one or more electron transport-mediating compounds under essentially aerobic conditions and absent reductase and B components from the same or other soluble methane monooxygenase, until at least a portion of the corresponding oxidized product is produced in an isolable amount, wherein said source of electrons and said electron transport-mediating compounds are able to reduce said hydroxylase.

2. The method for oxidizing hydrocarbons of claim 1 wherein said source of electrons is a chemical reductant.

3. The method for oxidizing hydrocarbons of claim 1 wherein said hydrocarbons are one or more members of the group consisting of alkanes, alkenes and aromatic hydrocarbons.

4. The method for oxidizing hydrocarbons of claim 2 wherein said hydroxylase is obtained from the bacterium *Methylosinus trichosporium* OB3b.

5. The method for oxidizing hydrocarbons of claim 4 wherein said hydrocarbons consist essentially of methane.

6. The method for oxidizing hydrocarbons of claim 2 wherein said hydroxylase is obtained from the bacterium *Methylosinus trichosporium* OB3b.

7. The method for oxidizing hydrocarbons of claim 1 wherein said source of electrons is a photochemical means for generating electrons.

8. The method for oxidizing hydrocarbons of claim 1 wherein said hydroxylase is obtained from the bacterium *Methylosinus trichsporium* OB3b.

9. The method for oxidizing hydrocarbons of claim 1 wherein said hydrocarbon is essentially methane.

10. The method for oxidizing hydrocarbons of claim 9 wherein said hydroxylase is obtained from the bacterium *Methylosinus trichosporium* OB3b.

11. The method for oxidizing hydrocarbons of claim 1 wherein the source of electrons is an electrochemical means for generating electrons.

12. The method for oxidizing hydrocarbons of claim 11 wherein said hydroxylase is obtained from bacterium *Methylosinus trichosporium* OB3b.

13. The method for oxidizing hydrocarbons of claim 12 wherein said hydrocarbon is essentially methane.

14. The method for oxidizing hydrocarbons of claim 1 wherein said hydroxylase contains at least about 3.5 mols of iron per mol of protein and has a final specific activity of at least about 800.

15. The method for oxidizing hydrocarbons of claim 14 wherein said source of electrons is a chemical reductant.

16. The method for oxidizing hydrocarbons of claim 4 wherein said hydroxylase is obtained from the bacterium *Methylosinus trichosporium* OB3b.

17. The method for oxidizing hydrocarbons of claim 16 wherein said hydrocarbons are essentially methane.

18. The method for oxidizing hydrocarbons of claim 4 wherein said hydroxylase contains at least about 4.0 mols iron per mol of protein and has a final specific activity of at least about 1000.

19. The method for oxidizing hydrocarbons of claim 18 wherein said hydroxylase is obtained from the bacterium *Methylosinus trichosporium* OB3b.

20. The method for oxidizing hydrocarbons of claim 19 wherein said hydrocarbons are essentially methane.

21. The method for oxidizing hydrocarbons of claim 16 wherein said source of electrons is a photochemical means for generating electrons.

22. The method for oxidizing hydrocarbons of claim 6 wherein said hydroxylase is obtained from the bacterium *Methylosinus trichosporium* OB3b.

23. The method for oxidizing hydrocarbons of claim 22 wherein said hydrocarbons are essentially methane.

24. The method for oxidizing hydrocarbons of claim 1 wherein said hydroxylase contains at least about 4.0 mols iron per mol protein and has a final specific activity of at least about 1000.

25. The method for oxidizing hydrocarbons of claim 24 wherein said hydroxylase is obtained from the bacterium *Methylosinus trichosporium* OB3b.

26. The method for oxidizing hydrocarbons of claim 25 wherein said hydrocarbons are essentially methane.

27. The method for oxidizing hydrocarbons of claim 14 wherein said source of electrons is an electrochemical means for generating electrons.

28. The method for oxidizing hydrocarbons of claim 8 wherein said hydroxylase is obtained from the bacterium *Methylosinus trichosporium* OB3b.

29. The method for oxidizing hydrocarbons of claim 28 wherein said hydrocarbons are essentially methane.

30. The method for oxidizing hydrocarbons of claim 8 wherein said hydroxylase contains at least about 4.0 mols iron per mol protein and a final specific activity of at least about 1000.

31. The method for oxidizing hydrocarbons of claim 30 wherein the hydroxylase is obtained from the bacterium *Methylosinus trichosporium* OB3b.

32. The method for oxidizing hydrocarbons of claim 30 wherein said hydrocarbons are essentially methane.

33. The method for oxidizing hydrocarbons of claim 2 wherein said electron transport compounds are one or more members of the group consisting of substituted viologen compounds and proflavin.

34. The method for oxidizing hydrocarbons of claim 3 wherein said chemical reductant is sodium dithionite and said electron transport compound is methyl viologen.

35. The method for oxidizing hydrocarbons of claim 7 wherein said electron transport compounds are one or more members of the group consisting of substituted viologen compounds and proflavin.

36. The method for oxidizing hydrocarbons of claim 35 wherein said electron transport compound is methyl viologen.

37. The method for oxidizing hydrocarbons of claim 11 wherein said electron transport compounds are one or more members of the group consisting of substituted methyl viologen compounds and proflavin.

38. The method for oxidizing hydrocarbons of claim 7 wherein said electron transport compound is methyl viologen.

39. The method for oxidizing hydrocarbons of claim 15 wherein said electron transport compounds are one or more members of the group consisting of substituted viologen compounds and proflavin.

40. The method for oxidizing hydrocarbons of claim 35 wherein said chemical reductant is sodium dithionite and said electron transport compound is methyl viologen.

41. The method for oxidizing hydrocarbons of claim 21 wherein said electron transport compounds are one or more members of the group consisting of substituted viologen compounds and proflavin.

42. The method for oxidizing hydrocarbons of claim 41 wherein said electron transport compound is methyl viologen.

43. The method for oxidizing hydrocarbons of claim 27 wherein said electron transport compounds are one or more members of the group consisting of substituted viologen compounds and proflavin.

44. The method for oxidizing hydrocarbons of claim 47 wherein said electron transport compound is methyl viologen.

45. The method for oxidizing hydrocarbons of claim 1 wherein said hydrocarbons are substituted hydrocarbons.

46. The method for oxidizing hydrocarbons of claim 14 wherein said hydrocarbons are substituted hydrocarbons.

* * * * *

UNITED STATES PATENT AND TRADEMARK OFFICE
CERTIFICATE OF CORRECTION

PATENT NO. : 5,190,870  
DATED : March 2, 1993  
INVENTOR(S) : John D. Lipscomb, et al Page 1 of 9

It is certified that error appears in the above-indentified patent and that said Letters Patent is hereby corrected as shown below:

| Col. | Line | |
|---|---|---|
| 6 | 52 | "The cell paste (300g)" should read --The cell paste (200g)-- |
| 14 | 60 | Tables I, II, III, IV(a), IV(B) and V should be inserted, as follows: |

UNITED STATES PATENT AND TRADEMARK OFFICE
CERTIFICATE OF CORRECTION

PATENT NO. : 5,190,870

DATED : March 2, 1993

INVENTOR(S) : John D. Lipscomb, et al

Page 2 of 9

It is certified that error appears in the above-indentified patent and that said Letters Patent is hereby corrected as shown below:

Col.      Line

TABLE I

SUMMARY OF THE PURIFICATION OF METHANE MONOOXYGENASE FROM METHYLOSINUS TRICHOSPORIUM OB3b[a]

| Step | Volume ml | Total Protein mg | Total Activity mUnits[b] | Specific Activity mUnits/mg | Yield % | Fold Purification |
|---|---|---|---|---|---|---|
| Hydroxylase | | | | | | |
| Cell free extract | 630 | 11150 | 2230000 | 200 | 100 | 1.0 |
| DEAE-Sepharose CL-6B | 177 | 1590 | 1427000 | 900 | 64 | 4.5 |
| Sephacryl S-300 | 95 | 835 | 1420000 | 1700 | 63 | 8.5 |
| Component B | | | | | | |
| Cell free extract | 630 | 11150 | 2230000 | 200 | 100 | 1.0 |
| DEAE Sepharose CL-6B | 169 | 590 | 1410000 | 2400 | 63 | 12.0 |
| Sephadex G-50 | 118 | 153 | 2563000 | 16700 | 115 | 83.5[c] |
| DEAE Sepharose CL-6B | 62 | 110 | 1237000 | 11200 | 55 | 56.0 |
| Reductase | | | | | | |
| Cell free extract | 630 | 11150 | 835000 | 75 | 100 | 1.0 |
| DEAE Sepharose CL-6B | 160 | 136 | 708000 | 5200 | 85 | 69.3 |
| DEAE Sepharose CL-6B | 68 | 68 | 651000 | 9600 | 78 | 128.0 |
| Ultrogel AcA-54 | 18 | 21 | 550000 | 26100 | 66 | 348.0 |

[a] Results from separate purifications for each component were normalized to the total protein in the cell free extract obtained from 200 g cell paste.
[b] A unit is defined as the production of 1 μmol of propene oxide per minute.
[c] The further purification step is required to remove trace cytochrome contaminants.

UNITED STATES PATENT AND TRADEMARK OFFICE
CERTIFICATE OF CORRECTION

PATENT NO. : 5,190,870

DATED : March 2, 1993

INVENTOR(S) : John D. Lipscomb, et al

It is certified that error appears in the above-indentified patent and that said Letters Patent is hereby corrected as shown below:

Col.    Line

TABLE II

PHYSICAL PROPERTIES OF PURIFIED METHANE MONOOXYGENASES

|  | *Methylosinus trichosporium* OB3b[a] | *Methylococcus capsulatus* (Bath)[b,c] | *Methylobacterium species* CRL-26[d,e] |
|---|---|---|---|
| Hydroxylase | | | |
| $s_{20,w}$ (sec x $10^{13}$) | 14.2 | 13.5 | 9.8 |
| $D_{20,w}$ ($cm^2$/sec x $10^7$) | 4.3 | | |
| Stokes radius (Å) | 50.3 | 49.2 | |
| Subunit structure | $(\alpha\beta\gamma)_2$ | $(\alpha\beta\gamma)_2$ | $(\alpha\beta\gamma)_2$ |
| Subunit molecular weights (kDa) | 54.4, 43.0, 22.7 | 54, 42, 17 | 55, 40, 20 |
| Molecular weight (kDa) | | | |
|   sedimentation velocity | 252 | | 225 |
|   gel filtration | 245 | 210 | 220 |
|   estimated from SDS-PAGE | 241 | 226 | 230 |
| Fe content (mol/mol) | 4.3 | 2.3 | 2.8 |
| Specific activity | 1700 | 72 | 208 |
| % recovery | 63 | 8 | 80 |
| mg obtained/200 g cell paste | 835 | 156 | 800 |
| Component B | | | |
| $s_{20,w}$ (sec x $10^{13}$) | 1.6 | | |
| $D_{20,w}$ ($cm_2$/sec x $10^7$) | 10.9 | | |
| Stokes radius (Å) | 19.6 | | |
| Molecular weight (kDa) | | | |
|   sedimentation velocity | 15.1 | | |
|   gel filtration | 15-31 | 17 | |
|   SDS-PAGE | 15.8 | 15.7 | |
| Metal content | none | none | |
| Specific activity | 11200 | 7300 | |
| pI | 4.3 | 4 | |
| % recovery | 55 | 36 | |
| mg obtained/200 g cell paste | 110 | 20 | |

UNITED STATES PATENT AND TRADEMARK OFFICE
CERTIFICATE OF CORRECTION

PATENT NO. : 5,190,870

DATED : March 2, 1993

INVENTOR(S) : John D. Lipscomb, et al

It is certified that error appears in the above-indentified patent and that said Letters Patent is hereby corrected as shown below:

Col.  Line

Reductase

| | | | |
|---|---|---|---|
| $s_{20,w}$ (sec x $10^{13}$) | 3.2 | | 2.1 |
| $D_{20,w}$ (cm2/sec x $10^7$) | 8.2 | | |
| Stokes radius (Å) | 26.2 | | |
| Molecular weight (kDA) | | | |
| sedimentation velocity | 38.4 | | 38 |
| gel filtration | 38.3 | 44.6 | 40 |
| SDS-PAGE | 39.7 | 39 | 40 |
| FAD (mol/mol) | 1 | 1 | 1 |
| Fe content (mol/mol) | 2 | 2 | 2 |
| Inorganic S content (mol/mol) | 2 | 2 | 2 |
| Specific activity | 26100 | 6000 | 6200 |
| % recovery | 66 | 35 | 48 |
| mg obtained/200 g cell paste | 21 | 248 | 18 | a  Typical cell yield 18-25 g cell paste per liter of culture media
b  Typical cell yield estimated to be 20 g cell paste per liter of culture media
c  See Woodland et al (J. Biol. Chem. 259, 53-59, 1984), Green et al. (J. Biol. Chem. 260, 15795-15801, 1985) and Colby et al. (Biochem. J. 177, 903-908, 1979) for methods used to determine physical properties
d  Typical cell yield 2-3 g cell paste per liter of culture media
e  See Patel et al. (J. Bact. 169, 2313-2317, 1987) and Patel (Arch. Biochem. Biophys. 252, 229-236, 1987) for methods used to determine physical properties

UNITED STATES PATENT AND TRADEMARK OFFICE
CERTIFICATE OF CORRECTION

PATENT NO. : 5,190,870

DATED : March 2, 1993

INVENTOR(S) : John D. Lipscomb, et al

Page 5 of 9

It is certified that error appears in the above-indentified patent and that said Letters Patent is hereby corrected as shown below:

Col.   Line

TABLE III
IRON CONTENT OF THE METHANE MONOOXYGENASE HYDROXYLASE

| Preparation | Specific Activity | Total Iron[a] | Mössbauer [oxo-center]/ [protein][b] | EPR mixed valent signal[c] | EPR g = 15 signal[d] |
|---|---|---|---|---|---|
| | nmol/min/mg | mol/mol | | spins/mol | mm |
| 1 | 70 | 1.9 | 0.91 | 0.66 | 13.5 |
| 2 | 70 | 2.1 | -- | 0.07* | 13.2 |
| 3 | 300 | 2.3 | 0.82 | 0.45 | 19.3 |
| 4 | 525 | 7.6 | 0.80 | 0.33 | -- |
| 5 | 900 | 4.3 | 1.56 | -- | -- |
| 6 | 1000 | 4.8 | -- | 1.30e | 22.6 |
| 7 | 1500 | 5.5 | -- | 0.15 | 27.3 |
| 8 | 1700 | 4.3 | 1.79 | 0.52 | 33.1 |

[a] Measured colorimetrically by complexation with 2,4,6-tripyridyl-s-triazine

[b] Estimated from the intensity of the diamagentic material present in the oxidized hydroxylase prepared from M. trichosporium OB3b cells grown on media enriched with $^{57}$Fe (2.3 mg/liter) as observed by Mössbauer spectroscopy, unreported samples were $^{56}$Fe hydroxylase preparations

[c] Measured by double integration of the mixed valent signal produced by chemical reduction with sodium dithionite, except for preparations marked "*," which were produced by NADH reduction in the presence of catalytic amounts of component B and reductase

[d] Estimated by measurement of the peak to trough displacement of the g = 15 signal observed upon complete reduction

[e] From five samples, the range of values was 0.6 to 1.3 spins per mol with an average value of 0.70; for NADH reduction, 0.13 spin per mol was observed

UNITED STATES PATENT AND TRADEMARK OFFICE
CERTIFICATE OF CORRECTION

PATENT NO. : 5,190,870

DATED : March 2, 1993

INVENTOR(S) : John D. Lipscomb, et al

It is certified that error appears in the above-indentified patent and that said Letters Patent is hereby corrected as shown below:

Col.     Line

TABLE IV(A)

SINGLE TURNOVER REACTIONS CATALYZED BY THE HYDROXYLASE COMPONENT OF METHANE MONOOXYGENASE

|  | Hydroxylation of Propene | | Hydroxylation of Propane | |
|---|---|---|---|---|
|  | nmol propene oxide | % yield[2] | nmol 1-propanol | % yield[2] |
| Reduced hydroxylase[1] | 80.2 | 40.1 | 20.3 | 10.1 |
| plus 200 nmol component B | 83.8 | 41.9 | 9.0 | 4.5 |
| plus 50 nmol reductase | 93.0 | 46.5 | NA* | -- |
| Mixed valent hydroxylase | 6.9 | 6.9 | 2.9 | 2.9 |
| plus 200 nmol component B | 7.4 | 7.4 | 3.6 | 3.6 |
| Redox mediators alone | 0 | 0 | 0 | 0 |
| Heat precipitated hydroxylase | 0 | 0 | 0 | 0 |
| 50 nmol reductase | 0 | 0 | NA | -- |
| 200 nmol component B | 0 | 0 | 0 | 0 |
| Hydroxylase, 500 μmol NADH | 0 | 0 | 0 | 0 |

Single turnover experiments were performed as described in the "Experimental Procedures."

* NA - not attempted
[1] 100 nmol hydroxylase with specific activity of 1000 mUnits/mg.
[2] Yield is calculated per binuclear iron center. The high activity hydroxylase used here was determined to have two centers (four irons per mol) (see Table III).

UNITED STATES PATENT AND TRADEMARK OFFICE
CERTIFICATE OF CORRECTION

PATENT NO. : 5,190,870

DATED : March 2, 1993

INVENTOR(S) : John D. Lipscomb, et al

It is certified that error appears in the above-indentified patent and that said Letters Patent is hereby corrected as shown below:

Col.   Line

TABLE IV(B)

REACTIONS CATALYZED BY THE HYDROXYLASE
COMPONENT OF METHANE MONOOXYGENASE

|  | Hydroxylation of Methane | | Hydroxylation of Benzene | |
|---|---|---|---|---|
|  | nmol methanol | % yield[2] | nmol phenol | % yield[2] |
| Reduced hydroxylase[1] |  |  |  |  |
| 340 nmol | 61 | 18 |  |  |
| 400 nmol |  |  | 14 | 3.5 |

All experiments were performed as described in the "Experimental Procedures."

* NA - not attempted
[1] Specific activity 155 mUnits/mg
[2] Yield is calculated per binuclear iron center. The low activity hydroxylase used here was determined to have one center (two irons per mol) (see Table III).

UNITED STATES PATENT AND TRADEMARK OFFICE
CERTIFICATE OF CORRECTION

PATENT NO. : 5,190,870  
DATED : March 2, 1993  
INVENTOR(S) : John D. Lipscomb, et al Page 8 of 9

It is certified that error appears in the above-indentified patent and that said Letters Patent is hereby corrected as shown below:

Col.  Line

TABLE V

MULTIPLE TURNOVER REACTIONS CATALYZED BY THE HYDROXYLASE COMPONENT OF METHANE MONOOXYGENASE

| Cycle | Specific Activity mUnits/mg | Hydroxylation of Propene | |
|---|---|---|---|
| | | nmol propene oxide | % yield[i] |
| -- | 151 | -- | -- |
| 1 | 152 | 116 | 34 |
| 2 | 162 | 126 | 71 |
| 7 | ND* | 533 | 157 |

UNITED STATES PATENT AND TRADEMARK OFFICE
CERTIFICATE OF CORRECTION

PATENT NO. : 5,190,870
DATED : March 2, 1993
INVENTOR(S) : John D. Lipscomb, et al It is certified that error appears in the above-indentified patent and that said Letters Patent is hereby corrected as shown below:

Multiple turnover experiments were performed as in the "Experimental Procedures."

[1] Yield is calculated per binuclear iron center. The low activity hydroxylase used here was determined to have about one center (two irons per mol) (see Table III).

* ND - Not determined

Signed and Sealed this

Twenty-seventh Day of September, 1994

Attest:

Attesting Officer

BRUCE LEHMAN

Commissioner of Patents and Trademarks